United States Patent

Eder et al.

(10) Patent No.: US 10,624,826 B2
(45) Date of Patent: *Apr. 21, 2020

(54) ANTIMICROBIAL COMPOSITIONS CONTAINING CATIONIC ACTIVE INGREDIENTS AND QUATERNARY SUGAR DERIVED SURFACTANTS

(71) Applicant: Ecolab USA Inc., Saint Paul, MN (US)

(72) Inventors: Angela R. Eder, St. Paul, MN (US); Daniel E. Pedersen, Cottage Grove, MN (US); Charles Allen Hodge, Cottage Grove, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/748,848

(22) Filed: Jun. 24, 2015

(65) Prior Publication Data

US 2015/0290100 A1   Oct. 15, 2015

Related U.S. Application Data

(63) Continuation of application No. 13/238,824, filed on Sep. 21, 2011, now Pat. No. 9,095,134.

(Continued)

(51) Int. Cl.
*C11D 1/62* (2006.01)
*C11D 1/75* (2006.01)
(Continued)

(52) U.S. Cl.
CPC ............... *A61K 8/43* (2013.01); *A01N 25/16* (2013.01); *A01N 25/30* (2013.01); *A01N 33/12* (2013.01);
(Continued)

(58) Field of Classification Search
CPC .. C11D 1/622; C11D 1/62; C11D 1/75; C11D 1/835; C11D 1/88; C11D 1/94;
(Continued)

(56) References Cited

U.S. PATENT DOCUMENTS 4,567,174 A   1/1986 Edwards et al.
5,188,756 A   2/1993 Baker
(Continued)

FOREIGN PATENT DOCUMENTS

EP   01028161 A1   8/2000
EP   1669061 B1    6/2006
(Continued)

OTHER PUBLICATIONS

CCI, "Poly Suga Quat Series—Natural, Green Conditioning Surfactants", 4 pages. Dec. 31, 2007.
(Continued)

*Primary Examiner* — Gregory R Delcotto
(74) *Attorney, Agent, or Firm* — McKee, Voorhees & Sease, PLC

(57) ABSTRACT

The antimicrobial composition of the present invention comprises a cationic active ingredient, a quaternized sugar-derived surfactant, and an optional foam boosting surfactant. The present antimicrobial compositions are free of the antimicrobial agent triclosan (i.e., 2,4,4'-trichloro-2'hydroxy-diphenylether), have a high cidal activity in a short amount of time, provide stable copious foam and exhibit enhanced tissue (e.g. skin) compatibility as defined by an in vitro whole toxicology assessment method.

17 Claims, 7 Drawing Sheets

Related U.S. Application Data

(60) Provisional application No. 61/385,341, filed on Sep. 22, 2010.

(51) Int. Cl.

| | | |
|---|---|---|
| *C11D 1/835* | (2006.01) | |
| *C11D 3/22* | (2006.01) | |
| *A61K 8/43* | (2006.01) | |
| *C11D 3/30* | (2006.01) | |
| *C11D 1/88* | (2006.01) | |
| *C11D 1/94* | (2006.01) | |
| *C11D 1/66* | (2006.01) | |
| *A61K 8/60* | (2006.01) | |
| *A01N 25/16* | (2006.01) | |
| *A01N 25/30* | (2006.01) | |
| *A01N 33/12* | (2006.01) | |
| *A01N 47/44* | (2006.01) | |
| *A61K 8/40* | (2006.01) | |
| *A61K 8/41* | (2006.01) | |
| *A61Q 17/00* | (2006.01) | |
| *A61Q 19/10* | (2006.01) | |

(52) U.S. Cl.
CPC ............. *A01N 47/44* (2013.01); *A61K 8/40* (2013.01); *A61K 8/416* (2013.01); *A61K 8/60* (2013.01); *A61K 8/604* (2013.01); *A61Q 17/005* (2013.01); *A61Q 19/10* (2013.01); *C11D 1/62* (2013.01); *C11D 1/662* (2013.01); *C11D 1/75* (2013.01); *C11D 1/835* (2013.01); *C11D 1/88* (2013.01); *C11D 1/94* (2013.01); *C11D 3/22* (2013.01); *C11D 3/30* (2013.01); *A61K 2800/30* (2013.01)

(58) Field of Classification Search
CPC .... C11D 3/22; C11D 3/30; B08B 3/04; B08B 3/08; B08B 3/10
USPC ....... 510/123, 124, 125, 127, 128, 130, 136, 510/137, 138, 470, 504; 424/70.19, 424/70.21, 70.24, 70.27; 134/42
See application file for complete search history.

(56) References Cited

U.S. PATENT DOCUMENTS

| | | |
|---|---|---|
| 5,234,618 A | 8/1993 | Kamegai |
| 5,376,686 A | 12/1994 | Ishikawa et al. |
| 5,415,814 A | 5/1995 | Ofosu |
| 5,417,893 A | 5/1995 | Ofosu |
| 5,653,970 A | 8/1997 | Vermeer |
| 5,707,959 A | 1/1998 | Pancheri |
| 5,756,446 A | 5/1998 | Bator |
| 6,057,274 A | 5/2000 | Bator |
| 6,221,828 B1 | 4/2001 | Matsuo |
| 6,323,171 B1 | 11/2001 | Fonsny |
| 6,384,004 B2 | 5/2002 | McCandlish |
| 6,387,866 B1 | 5/2002 | Mondin |
| 6,395,691 B1 | 5/2002 | Tsaur |
| 6,432,907 B1 | 8/2002 | Skold |
| 6,531,434 B1 | 3/2003 | Gluck |
| 6,730,654 B2 | 5/2004 | Godfroid et al. |
| 6,764,989 B1 | 7/2004 | Huish |
| 6,774,096 B1* | 8/2004 | Paye ...................... A61K 8/27 510/130 |
| 6,846,492 B2 | 1/2005 | Haap et al. |
| 6,946,786 B2 | 1/2005 | Patel |
| 6,881,710 B1 | 4/2005 | O'Lenick, Jr. et al. |
| 6,906,018 B1 | 6/2005 | Patel |
| 6,906,023 B1 | 6/2005 | Patel |
| 6,923,988 B2 | 8/2005 | Patel et al. |
| 7,084,129 B1 | 8/2006 | Smith et al. |
| 7,163,914 B2 | 1/2007 | Gluck |
| 7,179,779 B1 | 2/2007 | Hauser |
| 7,250,392 B1 | 7/2007 | Leonard |
| 7,345,015 B1 | 3/2008 | Kong et al. |
| 7,374,779 B2 | 5/2008 | Chen et al. |
| 7,501,387 B2 | 3/2009 | Aihara |
| 7,507,399 B1 | 3/2009 | O'Lenick, Jr. |
| 7,544,649 B2 | 6/2009 | Aihara |
| 7,547,672 B2 | 6/2009 | Zaki |
| 7,709,430 B2 | 5/2010 | Mizushima |
| 7,897,553 B2 | 3/2011 | Heiler |
| 9,095,134 B2* | 8/2015 | Eder .................. A01N 25/16 |
| 2002/0155978 A1 | 10/2002 | Man |
| 2002/0183233 A1 | 12/2002 | Shuman |
| 2003/0074742 A1 | 4/2003 | Perry |
| 2004/0136940 A1 | 7/2004 | Lazarowitz |
| 2005/0000030 A1 | 1/2005 | Dupont |
| 2005/0176614 A1 | 8/2005 | Soldanski |
| 2005/0215461 A1 | 9/2005 | Gluck et al. |
| 2006/0142174 A1 | 6/2006 | Fukuda |
| 2008/0161268 A1 | 7/2008 | Yen et al. |
| 2008/0209645 A1 | 9/2008 | Carrillo |
| 2009/0005281 A1* | 1/2009 | Hutton, III ............ A61K 8/41 510/125 |
| 2009/0069436 A1 | 3/2009 | MacGregor |
| 2010/0081596 A1 | 4/2010 | Rong |
| 2013/0035396 A1 | 2/2013 | Moen et al. |

FOREIGN PATENT DOCUMENTS

| | | |
|---|---|---|
| EP | 1669061 B9 | 3/2010 |
| JE | H10330793 A | 12/1998 |
| JP | H04325595 A | 11/1992 |
| JP | H09512052 T | 12/1997 |
| JP | H10508901 T | 9/1998 |
| JP | 2000297296 A | 10/2000 |
| JP | 2001525877 T | 12/2001 |
| JP | 2004224703 A | 8/2004 |
| JP | 2004526833 T | 9/2004 |
| JP | 2004315691 A | 11/2004 |
| JP | 2006028115 A | 2/2006 |
| JP | 2008266375 A | 11/2008 |
| WO | 1997030140 A1 | 8/1997 |
| WO | 2001007547 | 2/2001 |
| WO | 2006013315 | 2/2006 |
| WO | 2007101445 A1 | 9/2007 |
| WO | 2009029046 | 3/2009 |
| WO | 2010033562 | 3/2010 |

OTHER PUBLICATIONS

Viscardi, Guido, et al., "Synthesis and Surface and Antimicrobial Properties of Novel Cationic Surfactants", J. Org. Chem. 65, pp. 8197-8203. Oct. 28, 2000.

Claesson et al., "Sugar Surfactants", Encyclopedia of Surface and Colloid Science, Royal Institute of Technology, Stockholm, Sweden Aug. 15, 2006.

Simoes et al., "Action of a cationic surfactant on the activity and removal of bacterial biofilms formed under different flow regimes", Department of Biological Engineering, University of Minho, Gualtar, Portugal, vol. 39, Issues 2-3, pp. 478-486 Jan. 31, 2005.

Ecolab USA Inc., PCT/IB2011/054157, Application No./Patent No. 11826498.5-1454/2618806, "European Search Report", dated Jan. 31, 2014.

Coots, Robert J., New, Natural based Quaternary Conditioners for Personal Care Applications, Surfactant Spectator, p. 1-9, Jan. 31, 2009.

State Intellectual Property Office, "Rejection & Translation," issued in connection with Chinese Patent Application No. 2013-529751, dated Jul. 7, 2015, 13 pages.

State Intellectual Property Office, "Rejection & Translation," issued in connection with Chinese Patent Application No. 2013-528829, dated Jun. 2, 2015, 5 page.

\* cited by examiner

ANTIMICROBIAL COMPOSITIONS CONTAINING CATIONIC ACTIVE INGREDIENTS AND QUATERNARY SUGAR DERIVED SURFACTANTS

CROSS-REFERENCE TO RELATED APPLICATIONS

This is a Continuation Application of U.S. Ser. No. 13/238,824 filed Sep. 21, 2011, now U.S. Pat. No. 9,095,134, which claims priority to Provisional Application U.S. Ser. No. 61/385,341 filed on Sep. 22, 2010, all of which are herein incorporated by reference in their entirety.

FIELD OF THE INVENTION

The present invention is directed to antimicrobial compositions, like personal care compositions, having improved antimicrobial effectiveness and high foaming attributes. More particularly, the present invention relates to antimicrobial compositions exhibiting the antimicrobial effectiveness of cationic active ingredients and a polyquaternary functionalized alkyl polyglucoside or a quaternary functionalized alkyl polyglucoside, with optional properties of a broad spectrum of antimicrobial efficacy, high foam and reduced irritation to mammalian tissue.

BACKGROUND

Antimicrobial personal care compositions are known in the art. Especially useful are antimicrobial cleansing compositions, which typically are used to cleanse the skin and to destroy bacteria and other microorganisms present on the skin, especially the hands, arms, and face of the user.

Antimicrobial compositions are used, for example, in the health care industry; long term care, hospitality and health/exercise facilities; food service industry, meat processing industry, and in the private sector by individual consumers. The widespread use of antimicrobial compositions indicates the importance consumers place on controlling bacteria and other microorganism populations on skin. It is important, however, that antimicrobial populations provide a substantial and broad spectrum reduction in microorganism populations quickly and without problems associated with toxicity and skin irritation.

In particular, antimicrobial cleansing compositions typically contain an active antimicrobial agent, an anionic surfactant for cleansing and foam generation, skin conditioning agents for cosmetic effects, and dyes, perfumes, and optional thickening agents, such as clays, polymers, cellulosic derivatives, or colloids, for aesthetic effects, all in an aqueous carrier.

Several different classes of antimicrobial agents have been used in antimicrobial cleansing compositions. These include active ingredients selected from the following classes: phenolic compounds, carbanalide compounds, lower alcohols, surface active agents halogens, and carboxylic acids. Each of these classes has their own unique advantages and challenges. Examples of specific antimicrobial agents include PCMX (para-chrometa xylenol), Triclosan, Triclocarban, benzyl alcohol, quaternary ammonium compounds (QAC), iodine and iodine complexes and biguanides (e.g., chlorhexidine digluconate). At this time Triclosan is the dominant antimicrobial active ingredient in the dermal cleanser market.

Although there is an increasing consumer demand for products which have both an activity against bacteria and other microorganisms, there is an even greater demand to fulfill the consumer's expectations with regard to their level of concern with certain biocides such as Triclocarban and Triclosan.

Triclosan is disfavored as an antimicrobial agent due to environmental persistence and health concerns due to the possible formation of intermediate and/or environmental by products. Thus, a need exists for an efficacious antimicrobial personal care composition which is substantially free of biocides such as Triclocarban and Triclosan but that still provides a high foam level desired by consumers and is mild to the skin. The present invention is directed to such antimicrobial compositions.

The above-mentioned disadvantages of current antimicrobial compositions are addressed by embodiments of the present invention and will be understood by reading and studying the following specification. The following summary is made by way of example and not by way of limitation. It is merely provided to aid the reader in understanding some of the aspects of the invention.

SUMMARY OF THE INVENTION

The summary of the invention is intended to introduce the reader to various exemplary aspects of the invention. Particular aspects of the invention are shown in other sections herein below, and the invention is set forth in the appended claims which alone demarcate its scope.

In accordance with an exemplary embodiment of the present invention, an antimicrobial composition that exhibits fast efficacy and high foaming attributes is provided. The antimicrobial composition comprises a cationic active ingredient, a quaternized sugar-derived surfactant, a foam boosting surfactant which may encompass nonionic surfactants, amphoteric surfactants, cationic surfactants, anionic surfactants and water. The present antimicrobial compositions are free of the antimicrobial agent triclosan (i.e., 2,4,4'-trichloro-2'hydroxy-diphenylether), have a high cidal activity in a short amount of time, provide stable copious foam and may optionally contain ingredients to increase skin compatibility and skin health.

Accordingly, one aspect of the present invention is to provide an antimicrobial composition for reducing microbial population on dermal tissue, the antimicrobial composition comprising: (a) about 0.3 wt. % to about 6.0 wt. %, by weight of cationic actives; (b) about 0.1 wt. % to about 18 wt. %, by weight, of a quaternized sugar-derived surfactant; (c) about 0.1 wt. % to about 40 wt. %, by weight of a foam boosting surfactant; (d) about 1 wt. % to about 25 wt. % dermal adjuvants and (e) water or other suitable diluent.

Additionally, one aspect of the present invention is to provide an antimicrobial composition for reducing microbial population on dermal tissue, wherein the composition has a relative weight ratio of cationic active to quaternized sugar surfactant to foam boosting surfactant from about 1:0.2:0.2 to about 1:3:8.

Another aspect of the present invention is to provide an antimicrobial composition for reducing microbial population on dermal tissue which is stable and has a pH of about 4.0 to about 9.0. The present composition also exhibits excellent esthetic properties, such as copious foam and foam stability and may optionally contain ingredients to increase skin compatibility and skin health. Moreover, the composition may exhibit reduced tissue irritancy potential.

A further aspect of the present invention is to provide personal use products based on an antimicrobial composition of the present invention, for example, a skin cleanser, a surgical scrub, a hand sanitizer gel, a disinfectant, antiseptic wash, and the like.

A further aspect of the present invention is to provide a method of reducing Gram positive and/or Gram negative bacteria populations on mammalian tissue, including human tissue, by contacting the tissue, like the dermis, with a composition of the present invention for a sufficient time, such as about 30 seconds to 5 minutes, to reduce the bacteria level to a desired level. Antimicrobial efficacy is applicable to viral and fungal organisms as well as Gram positive and Gram negative bacteria.

While multiple embodiments are disclosed, still other embodiments of the present invention will become apparent to those skilled in the art from the following detailed description, which shows and describes illustrative embodiments of the invention. Accordingly, the detailed description is to be regarded as illustrative in nature and not restrictive.

DETAILED DESCRIPTION OF THE PREFERRED EMBODIMENTS

Figure 1:
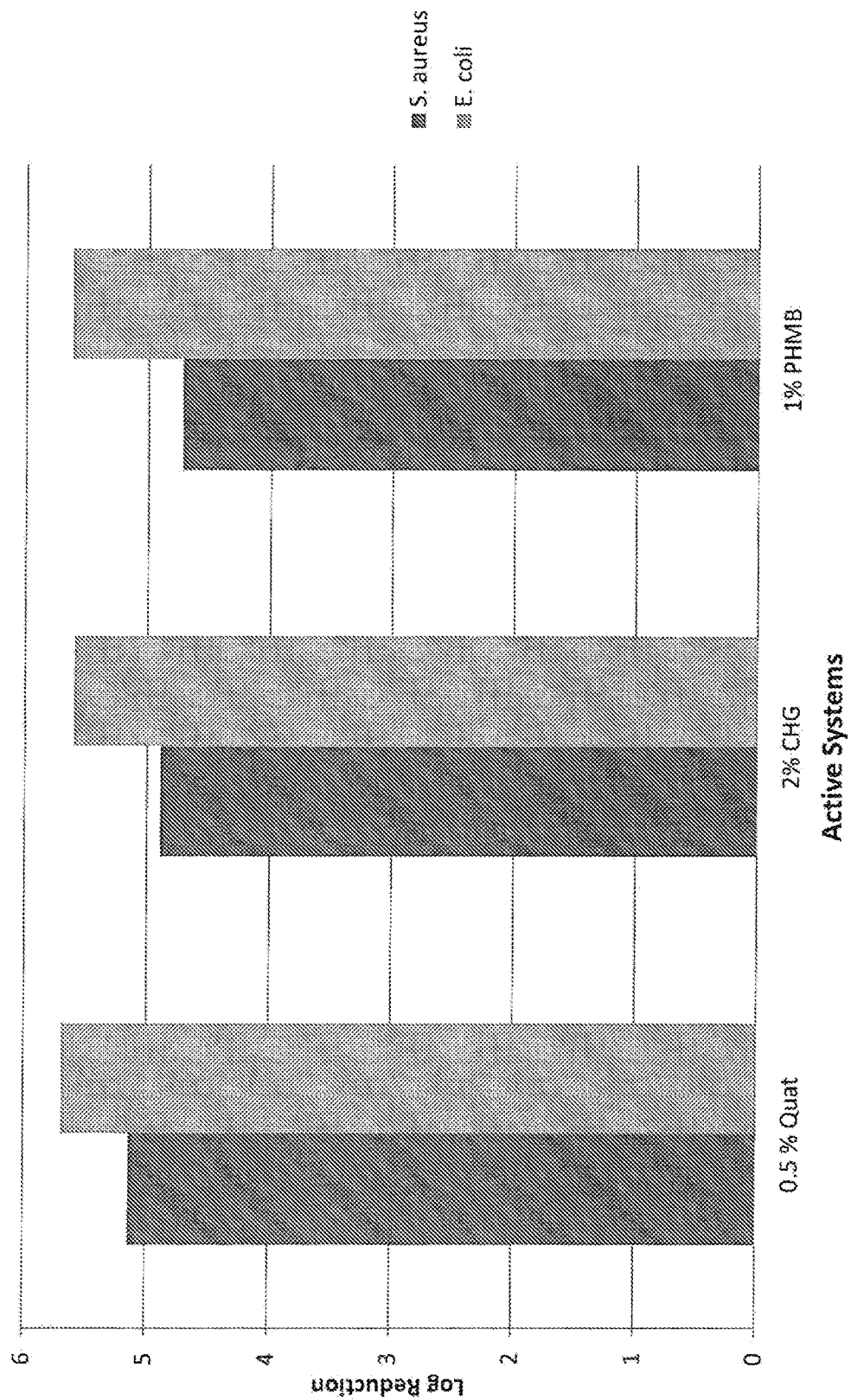
FIG. 1 illustrates a graph depicting the tests results of the efficacy following a 30 second exposure time of three different cationic active ingredients, specifically, 0.5% quat (benzalkonium chloride), 2% CHG (chlorhexidine gluconate), and 1% PHMB (polyhexamethylene biguanide) in a representative surfactant system.

Other than in the operating examples, or where otherwise indicated, all numbers expressing quantities of ingredients or reaction conditions used herein are to be understood as being modified in all instances by the term "about".

As used herein, weight percent (wt-%), percent by weight, % by weight, and the like are synonyms that refer to the concentration of a substance as the weight of that substance divided by the total weight of the composition and multiplied by 100.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities.

As used herein, the term "cationic active" is defined as the ingredient that provides antimicrobial cidal activity.

As used herein, the term "skin care active" is defined as the ingredient or ingredients that improve or maintain the health of the dermal barrier.

The term "alkyl" refers to a straight or branched chain monovalent hydrocarbon radical having a specified number of carbon atoms. As used herein, "alkyl" refer to a linear or branched $C_6$-$C_{18}$ carbon chain.

The term "microbial" or "microbial population" refers to bacterial, fungal, yeast, or viral population or combinations thereof or any mixture thereof in a laboratory or natural setting.

The term "surfactant" or "surface active agent" refers to an organic chemical that when added to a liquid changes the properties of that liquid at a surface or interface.

"Cleansing" means to perform or aid in soil removal, bleaching, microbial population reduction, rinsing, or combination thereof.

As used herein, the term "substantially free" refers to compositions completely lacking the component or having such a small amount of the component that the component does not affect the effectiveness of the composition. The component may be present as an impurity or as a contaminant and shall be less than 0.5 wt. %. In another embodiment, the amount of the component is less than 0.1 wt. % and in yet another embodiment, the amount of component is less than 0.01 wt. %.

It should be noted that, as used in this specification and the appended claims, the singular forms "a", "an", and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The term "actives" or "percent actives" or "percent by weight actives" or "actives concentration" are used interchangeably herein and refers to the concentration of those ingredients involved in cleansing expressed as a percentage minus inert ingredients such as water or salts.

As used herein, the terms "triclosan free" or "free of triclosan" refers to a composition, mixture, or ingredients that do not contain triclosan (2,4,4'-trichloro-2'hydroxydiphenylether) or triclosan containing compounds or to which the same has not been added. Should triclosan or triclosan containing compounds be present through contamination of a composition, mixture, or ingredients, the amount of the same shall be less than 0.5 wt. %. In another embodiment, the amount of is less than 0.1 wt. % and in yet another embodiment, the amount is less than 0.01 wt. %.

Antimicrobial Compositions Containing Cationic Active Compounds and Quaternized Sugar Derived Surfactants The present invention relates to an antimicrobial composition that exhibits fast efficacy and high foaming attributes. The antimicrobial composition comprises a cationic active ingredient, a quaternized sugar-derived surfactant, a foam boosting surfactant which may encompass anionic surfactants, nonionic surfactants, amphoteric surfactants, or cationic surfactants and water. The present antimicrobial compositions are free of the antimicrobial agent triclosan (i.e., 2,4,4'-trichloro-2'hydroxy-diphenylether), have a high cidal activity in a short amount of time, provide stable copious foam and may optionally contain ingredients to increase skin compatibility and skin health.

In one embodiment, an antimicrobial composition for reducing microbial population on dermal tissue includes: (a) about 0.3 wt. % to about 6.0 wt. %, by weight of cationic actives; (b) about 0.1 wt. % to about 18 wt. %, by weight, of a quaternized sugar-derived surfactant; (c) about 0.1 wt. % to about 40 wt. %, by weight of a foam boosting surfactant; (d) about 1 wt. % to about 25 wt. % dermal adjuvants and (e) water or other suitable diluent. The relative weight ratio of cationic active ingredient to quaternized sugar surfactant to foam boosting surfactant is from about 1:0.2:0.2 to about 1:3:8.

Another aspect of the present invention is to provide an antimicrobial composition for reducing microbial population on dermal tissue which is stable and has a pH of about 5.0 to about 8.0. The present composition also surprisingly exhibits excellent esthetic properties, such as copious foam and foam stability and may optionally contain ingredients to increase skin compatibility and skin health. Moreover, the composition may exhibit reduced tissue irritancy potential.

A further aspect of the present invention is to provide personal use products based on an antimicrobial composition of the present invention, for example, a skin cleanser, a surgical scrub, a hand sanitizer gel, a disinfectant, and the like.

A further aspect of the present invention is to provide a method of reducing Gram positive and/or Gram negative bacteria populations on mammalian tissue, including human tissue, by contacting the tissue, like the dermis, with a composition of the present invention for a sufficient time, such as about 30 seconds to 5 minutes, to reduce the bacteria level to a desired level.

The following illustrates non-limiting embodiments of the present invention.

A. Cationic Actives

A cationic active is present in an antimicrobial composition for reducing microbial population on the dermal tissue of a mammal of the present invention in an amount of about 0.3 wt. % to about 6.0 wt. %, and preferably about 0.5 wt. % to about 5.0 wt. %, by weight of the composition.

The amount of antimicrobial agent in the composition is related to the end use of the composition, the amount of quaternized sugar-derived surfactant and foam boosting surfactant in the composition, and the presence of optional ingredients in the composition. The amount of antimicrobial agent is sufficient to achieve a microbial kill in a short contact time, for example, 15 to 30 seconds.

Cationic active ingredients are an antimicrobial agent useful in the present invention. The cationic or cationically-active ingredients are substances based on nitrogen centered cationic moieties with net positive change. The cationic or cationically-active ingredients are preferably selected from the group consisting of cationic polymers, cationic surfactants, cationic monomers, cationic silicon compounds, cationic derivatized protein hydrolyzates and betaine with at least one cationic or cationically-active group.

Suitable cationic active ingredients contain quaternary ammonium groups. Suitable cationic active ingredients especially include those of the general formula:

wherein $R^1$, $R^2$, $R^3$ and $R^4$ independently of each other represent alkyl groups, aliphatic groups, aromatic groups, alkoxy groups, polyoxyalkylene groups, alkylamido groups, hydroxyalkyl groups, aryl groups, $H^+$ ions, each with from 1 to 22 carbon atoms, with the provison that at least one of the groups $R^1$, $R^2$, $R^3$ and $R^4$ has at least eight carbon atoms and wherein $X(-)$ represents an anion, for example, a halogen, acetate, phosphate, nitrate or alkyl sulfate, preferably a chloride. The aliphatic groups can also contain cross-linking or other groups, for example additional amino groups, in addition to the carbon and hydrogen atoms.

Particular cationic active ingredients include, for example, but are not limited to, alkyl dimethyl benzyl ammonium chloride (ADBAC), alkyl dimethyl ethylbenzyl ammonium chloride, dialkyl dimethyl ammonium chloride, benzethonium chloride, N, N-bis-(3-aminopropyl) dodecylamine, chlorhexidine gluconate, PHMB (polyhexamethylene biguanide), salt of a biguanide, a substituted biguanide derivative, an organic salt of a quaternary ammonium containing compound or an inorganic salt of a quaternary ammonium containing compound or mixtures thereof.

In accordance with an important feature of the present invention, a present antimicrobial composition is substantially free of triclosan. The phrase "substantially free" of triclosan is defined as meaning that the composition contains 0% to about 0.25% by weight, in total, of triclosan. In particular, triclosan may be present in an antimicrobial composition in a total amount of 0.25% or less either as a by-product or as a component of an ingredient in the composition, but triclosan is not intentionally introduced into the composition.

Triclosan is disfavored as an antimicrobial agent due to environmental and health concerns due to the possible formation of intermediate and/or environmental by products.

B. Quaternized Sugar-Derived Surfactant

In addition to an antimicrobial agent, the present antimicrobial composition for reducing microbial population on the dermal tissue of a mammal of the present invention also contains a quaternized sugar-derived surfactant. The quaternized sugar-derived surfactant is present in an amount of about 0.1% to about 18%, and preferably about 0.25% to about 12.5%, by weight, of the composition.

The amount of quaternized sugar-derived surfactant present in the composition is related to the amount of the cationic active in the composition, to the identity of the quaternized sugar-derived surfactant, and the end use of the composition.

The quaternized sugar-derived surfactant is a quaternized alkyl polyglucoside or a polyquaternized alkyl polyglucoside, and the like.

In one embodiment, the antimicrobial composition of the present invention includes a polyquaternary functionalized alkyl polyglucoside, a cationic active ingredient, water, and an optional foam boosting surfactant. The poly quaternary functionalized alkyl polyglucoside is a cationic surfactant naturally derived from alkyl polyglucosides and has a sugar backbone. Poly quaternary alkyl polyglucosides have the following representative formula:

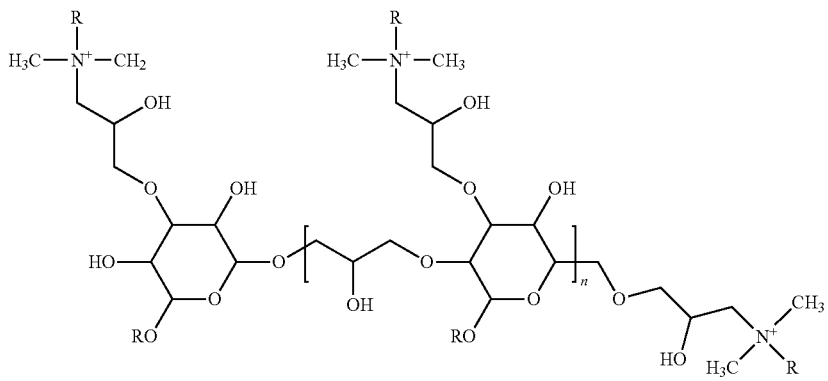

Wherein R is an alkyl group having from about 6 to about 22 carbon atoms and n is an integer ranging from 4 to 6. Examples of suitable poly quaternary functionalized alkyl polyglucosides components which can be used in the cleansing compositions according to the present invention include those in which the R alkyl moiety contains from about 8 to about 12-carbon atoms. In a preferred embodiment the quaternary functionalized alkyl polyglucoside contains primarily about 10-12 carbon atoms. Examples of commercially suitable poly quaternary functionalized alkyl polyglucosides useful in cleansing compositions of the present invention include but is not limited to: Poly Suga® Quat series of quaternary functionalized alkyl polyglucosides, available from Colonial Chemical, Inc., located in South Pittsburgh, Tenn.

In another embodiment, the antimicrobial composition of the present invention includes a quaternary functionalized alkyl polyglucoside, a cationic active ingredient, water, and an optional foam boosting surfactant. The quaternary functionalized alkyl polyglucoside is a naturally derived cationic surfactant from alkyl polyglucosides and has a sugar backbone. Quaternary functionalized alkyl polyglucosides have the following representative formula:

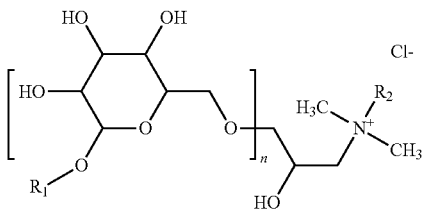

Wherein $R_1$ is an alkyl group having from about 6 to about 22 carbon atoms, and $R_2$ is $CH_3(CH_2)_{n'}$ where n' is an integer ranging from 0-21. Examples of suitable quaternary functionalized alkyl polyglucosides components which can be used in the cleansing compositions according to the present invention include those in which the $R_1$ alkyl moiety contains primarily about 10-12 carbon atoms, the $R_2$ group is $CH_3$ and n is the degree of polymerization of 1-2. Further examples of a suitable quaternary functionalized alkyl polyglucoside include, but are not limited to, the antimicrobial and antifungal quaternary functionalized alkyl polyglucosides described in U.S. Pat. Nos. 7,084,129 and 7,507,399 the disclosures of which are hereby incorporated by reference. Examples of commercially suitable quaternary functionalized alkyl polyglucosides useful in cleansing compositions of the present invention include but is not limited to: Suga® Quat TM 1212 (primarily $C_{12}$ quaternary functionalized alkyl polyglucoside), Suga® Quat L 1210 (primarily $C_{12}$ quaternary functionalized alkyl polyglucoside), and Suga® Quat S 1218 (primarily $C_{12}$ quaternary functionalized alkyl polyglucoside) available from Colonial Chemical, Inc., located in South Pittsburgh, Tenn.

C. Foam-Boosting Co-Surfactant

In addition to an antimicrobial agent, and a quaternized sugar-derived surfactant the present antimicrobial composition for reducing microbial population on the dermal tissue of a mammal of the present invention also contains a foam boosting surfactant. The foam booting surfactant is present in an amount of about 0.02% to about 10.0%, and preferably about 2% to about 6%, by weight, of the composition.

The amount of foam boosting surfactant present in the composition is related to the amount of the cationic active in the composition, the amount of the quaternized sugar-derived surfactant in the composition, the identity of the foam boosting surfactant, and the end use of the composition.

The foam-boosting co-surfactant can be (a) nonionic surfactants, (b) amphoteric surfactants, (c) cationic surfactants, (d) anionic surfactants and the like, or (e) mixtures thereof.

Non Ionic Foam Boosting Surfactant

Examples of non ionic foam-boosting co-surfactants include, but are not limited to, alkyl amine oxide, alkyl ether amine oxide, alkyl alcohol alkoxylates, aryl alcohol alkoxylates, substituted alcohol alkoxylates, block nonionic copolymers, heteric nonionic copolymers, alkanolamides, substituted amides, or polyethoxylated glycerol derivatives.

The antimicrobial composition can contain a nonionic surfactant component that includes a detersive amount of nonionic surfactant or a mixture of nonionic surfactants. Typically, a nonionic surfactant has a hydrophobic region, such as a long chain alkyl group or an alkylated aryl group, and a hydrophilic group comprising an ethoxy and/or other hydrophilic moieties. As defined herein, a "nonionic foam-boosting co-surfactant" has a hydrophobic region having an alkyl group containing six to eighteen carbon atoms, and an average of one to about twenty ethoxy and/or propoxy moieties. Examples of non ionic foam-boosting co-surfactants include, but are not limited to, alkyl amine oxide, alkyl ether amine oxide, alkyl alcohol alkoxylates, aryl alcohol alkoxylates, substituted alcohol alkoxylates, block nonionic copolymers, heteric nonionic copolymers, alkanolamides, or polyethoxylated glycerol esters, and mixtures thereof.

Numerous other nonionic surfactants are disclosed in McCutcheon's Detergents and Emulsifiers, 1993 Annuals, published by McCutcheon Division, MC Publishing Co., Glen Rock, N.J., pp. 1-246 and 266-273; in the *CTFA International Cosmetic Ingredient Dictionary, Fourth Ed.*, Cosmetic, Toiletry and Fragrance Association, Washington, D.C. (1991) (hereinafter the *CTFA Dictionary*) at pages 1-651; and in the *CTFA Cosmetic Ingredient Handbook, First Ed.*, Cosmetic, Toiletry and Fragrance Association, Washington, D.C. (1988) (hereafter the *CTFA Handbook*), at pages 86-94, each incorporated herein by reference.

Amphoteric Foam Boosting Surfactant

The antimicrobial composition can contain an amphoteric surfactant component that includes a detersive amount of amphoteric surfactant or a mixture of amphoteric surfactants. Suitable amphoteric surfactants that can be used include, but are not limited to, imidiazolines and imidiazoline derivatives, isethionates, betaine derivatives, amphoacetate derivatives, propionates, and mixtures thereof.

Anionic Foam Boosting Surfactant

The antimicrobial composition can contain an anionic surfactant component that includes a detersive amount of an anionic surfactant or a mixture of anionic surfactants. The anionic surfactants that can be used according to the invention include any anionic surfactant available in the cleansing industry. Suitable groups of anionic surfactants include sulfonates and sulfates. Suitable surfactants that can be provided in the anionic surfactant component include, but are not limited to, sarcosine derivatives, succinic acid derivatives, carboxylated alcohols, alkyl sulfate and alkyl ether sulfates, sulfonic acid derivatives, diphenyll sulfonate derivatives, alkyl aryl sulfonic acid derivatives, alkyl polyglucoside sulfates or sulfonates.

Cationic Foam Boosting Surfactant

The antimicrobial composition may contain a cationic surfactant component that includes a detersive amount of cationic surfactant or a mixture of cationic surfactants. Cationic surfactants that can be used in the antimicrobial composition include, but are not limited to, quaternized polysaccharides, alkyl polysaccharides, alkoxylated amines, alkoxylated ether amines, phospholipids, phospholipid derivatives, and mixtures thereof.

D. Carrier

The carrier of the present antimicrobial composition comprises water, propylene glycol, glycerols, alcohols or mixtures thereof. It should be appreciated that the water may be provided as deionized water or as softened water. The water provided as part of the concentrate can be relatively free of hardness. It is expected that the water can be deionized to remove a portion of the dissolved solids. That is, the concentrate can be formulated with water that includes dissolved solids, and can be formulated with water that can be characterized as hard water.

The antimicrobial composition of the present invention does not rely upon a low pH or a high pH to provide a rapid reduction in microbial populations. Antimicrobial populations of the present invention have a pH of about 5.0 to about 8.0. Within this pH range, the present compositions effectively reduce microbial populations, and are consumer acceptable, i.e., are mild to the skin, are phase stable, and generate copious, stable foam.

E. Additional Functional Materials

The antimicrobial composition can include additional components or agents, such as additional functional materials. As such, in some embodiments, the antimicrobial composition including the cationic active ingredients and quaternary sugar-derived surfactants may provide a large amount, or even all of the total weight of the antimicrobial composition, for example, in embodiments having few or no additional functional materials disposed therein. The functional materials provide desired properties and functionalities to the antimicrobial composition. For the purpose of this application, the term "functional materials" include a material that when dispersed or dissolved in a use and/or concentrate solution, such as an aqueous solution, provides a beneficial property in a particular use. The antimicrobial composition containing the cationic active ingredients and the quaternized sugar-derived surfactants may optionally contain other disinfectants, sanitizers, dyes, thickening or gelling agents, and perfumes. Some particular examples of functional materials are discussed in more detail below, but it should be understood by those of skill in the art and others that the particular materials discussed are given by way of example only, and that a broad variety of other functional materials may be used. For example, may of the functional material discussed below relate to materials used in disinfecting and/or cleansing applications, but it should be understood that other embodiments may include functional materials for use in other applications.

Dyes and Fragrances

Various dyes, odorants including perfumes, and other aesthetic enhancing agents which are compatible with the invention chemistry may also be included in the antimicrobial composition.

Fragrances or perfumes that may be included in the compositions include, for example, terpenoids such as citronellol, aldehydes such as amyl cinnamaldehyde, a jasmine such as C1S-jasmine or jasmal, vanillin, and the like.

Adjuvants

The present composition can also include any number of adjuvants. In one embodiment adjuvants are present in an amount of about 1% to about 25%, and preferably about 1% to about 15%, by weight, of the composition, Specifically, the antimicrobial composition can include glycerin, sorbitol, esters, polyquats, glycols, preservatives, chelators, pH additives, pigments or dyes among any number of other constituents which can be added to the composition. Such adjuvants can be pre-formulated with the present composition or added to the system simultaneously, or even after, the addition of the present composition. The antimicrobial composition can also contain any number of other constituents as necessitated by the application, which are known and which can facilitate the activity of the present invention.

Embodiments of the Present Invention

The antimicrobial composition of the present invention has a high broad spectrum of antimicrobial efficacy, high foam and reduced irritation to mammalian tissue. Exemplary compositions are provided in the following tables.

Antimicrobial Dermal Cleanser

TABLE 1

Antimicrobial Dermal Wash Exemplary Composition (Expressed as Weight Percentage)
Antimicrobial Dermal Wash (pH 5.0-6.7)

| Ingredient | Example | Preferred Embodiment (% w/w) Lower Limit | Preferred Embodiment (% w/w) Upper Limit | Most Preferred Embodiment (% w/w) Lower Limit | Most Preferred Embodiment (% w/w) Upper Limit |
|---|---|---|---|---|---|
| Cationic Active Ingredient | Quaternary Ammonium Compound (QAC) [Alkyl Dimethyl Benzyl Ammonium Chloride (ADBAC)] | 0.4 | 1.5 | 0.5 | 1.0 |
| Quaternized Sugar-Derived Surfactant | Quaternary functionalized alkyl polyglucoside or Polyquaternary functionalized alkyl polyglucoside | 0.1 | 4.5 | 0.25 | 2.5 |
| Foam Boosting Surfactant | Dimethyl amine oxide; alkyl polyglucoside | 0.1 | 12.0 | 1.0 | 5.0 |
| Adjuvants (Dermal) | Glycerin, Sorbitol, Esters, Polyquats, Glycols, Preservative | 1.0 | 25.0 | 2.0 | 10.0 |

TABLE 2

Antimicrobial Dermal Wash Exemplary Composition (Expressed as Weight Ratio)
Antimicrobial Dermal Wash (pH 5.0-6.7)

| Ingredient | Example | Preferred Embodiment (Weight Ratio) Lower Limit | Preferred Embodiment (Weight Ratio) Upper Limit | Most Preferred Embodiment (Weight Ratio) Lower Limit | Most Preferred Embodiment (Weight Ratio) Upper Limit |
|---|---|---|---|---|---|
| Cationic Active Ingredient | Quaternary Ammonium Compound (QAC) [Alkyl Dimethyl Benzyl Ammonium Chloride (ADBAC)] | 1.0 | 1.0 | 1.0 | 1.0 |
| Quaternized Sugar-Derived Surfactant | Quaternary functionalized alkyl polyglucoside or Polyquaternary functionalized alkyl polyglucoside | 0.25 | 3.0 | 0.5 | 2.5 |
| Foam Boosting Surfactant | Dimethyl amine oxide; alkyl polyglucoside | 0.25 | 8.0 | 2.0 | 5.0 |
| Adjuvants (Dermal) | Glycerin, Sorbitol, Esters, Polyquats, Preservative | 2.5 | 16.0 | 4.0 | 10.0 |

TABLE 3

Dermal Cleanser Exemplary Composition (Expressed as Weight Percentage)
Dermal Cleanser (pH 5.5-7.5)

| Ingredient | Example | Preferred Embodiment (% w/w) Lower Limit | Preferred Embodiment (% w/w) Upper Limit | Most Preferred Embodiment (% w/w) Lower Limit | Most Preferred Embodiment (% w/w) Upper Limit |
|---|---|---|---|---|---|
| Cationic Active Ingredient | Quaternary Ammonium Compound (QAC) [Alkyl Dimethyl Benzyl Ammonium Chloride (ADBAC)] | 0.3 | 5.0 | 0.5 | 4.0 |
| Quaternized Sugar-Derived Surfactant | Quaternary functionalized alkyl polyglucoside or Polyquaternary functionalized alkyl polyglucoside | 0.1 | 15.0 | 0.25 | 10.0 |
| Foam Boosting Surfactant | Dimethyl amine oxide; alkyl polyglucoside | 0.1 | 40.0 | 2.0 | 20.0 |
| Adjuvants (Dermal) | Glycerin, Sorbitol, Esters, Polyquats, Preservative | 1.0 | 25.0 | 1.75 | 15.0 |

TABLE 4

Dermal Cleanser Exemplary Composition (Expressed as Weight Ratio)
Dermal Cleanser (pH 5.5-7.5)

| Ingredient | Example | Preferred Embodiment (% w/w) Lower Limit | Preferred Embodiment (% w/w) Upper Limit | Most Preferred Embodiment (% w/w) Lower Limit | Most Preferred Embodiment (% w/w) Upper Limit |
|---|---|---|---|---|---|
| Cationic Active Ingredient | Quaternary Ammonium Compound (QAC) [Alkyl Dimethyl Benzyl Ammonium Chloride (ADBAC)] | 1.0 | 1.0 | 1.0 | 1.0 |
| Quaternized Sugar-Derived Surfactant | Quaternary functionalized alkyl polyglucoside or Polyquaternary functionalized alkyl polyglucoside | 0.3 | 3.0 | 0.5 | 2.5 |
| Foam Boosting Surfactant | Dimethyl amine oxide; alkyl polyglucoside | 0.3 | 8.0 | 1.0 | 5.0 |
| Adjuvants (Dermal) | Glycerin, Sorbitol, Esters, Polyquats, Preservative | 3.3 | 5.0 | 3.5 | 3.75 |

TABLE 5

Surgical Scrub Exemplary Composition (Expressed as Weight Percentage) Surgical Scrub (pH 5.5-7.5)

| Ingredient | Example | Preferred Embodiment (% w/w) | | Most Preferred Embodiment (% w/w) | |
|---|---|---|---|---|---|
| | | Lower Limit | Upper Limit | Lower Limit | Upper Limit |
| Cationic Active Ingredient | Chlorhexidine Gluconate (CHG) | 1 | 6.0 | 1.5 | 5.0 |
| Quaternized Sugar-Derived Surfactant | Quaternary functionalized alkyl polyglucoside or Polyquaternary functionalized alkyl polyglucoside | 0.2 | 18.0 | 0.6 | 12.5 |
| Foam Boosting Surfactant | Dimethyl amine oxide; alkyl polyglucoside | 0.2 | 36.0 | 1.5 | 25.0 |
| Adjuvants (Dermal) | Glycerin, Sorbitol, Esters, Polyquats, Preservative | 1.0 | 25.0 | 2.0 | 10.0 |

TABLE 6

Surgical Scrub Exemplary Composition (Expressed as Weight Ratio) Surgical Scrub (pH 5.5-7.5)

| Ingredient | Example | Preferred Embodiment (% w/w) | | Most Preferred Embodiment (% w/w) | |
|---|---|---|---|---|---|
| | | Lower Limit | Upper Limit | Lower Limit | Upper Limit |
| Cationic Active Ingredient | Chlorhexidine Gluconate (CHG) | 1.0 | 1.0 | 1.0 | 1.0 |
| Quaternized Sugar-Derived Surfactant | Quaternary functionalized alkyl polyglucoside or Polyquaternary functionalized alkyl polyglucoside | 0.2 | 3.0 | 0.4 | 2.5 |
| Foam Boosting Surfactant | Dimethyl amine oxide; alkyl polyglucoside | 0.2 | 6.0 | 1.0 | 5.0 |
| Adjuvants (Dermal) | Glycerin, Sorbitol, Esters, Polyquats, Preservative | 1.0 | 4.2 | 1.3 | 2.0 |

The formula may be available as a ready-to-use or concentrate which would be subsequently diluted to the proper use concentration with water either manually or by suitable equipment or an apparatus. The concentrate composition of the present invention can be provided as a solid, liquid, or gel, or a combination thereof. In one embodiment, the cleansing compositions may be provided as a concentrate such that the cleansing composition is substantially free of any added water or the concentrate may contain a nominal amount of water The concentrate can be formulated without any water or can be provided with a relatively small amount of water in order to reduce the expense of transporting the concentrate. For example, the composition concentrate can be provided as a capsule or pellet of compressed powder, solid, or loose powder, either contained by a water soluble material or not. In the case of providing the capsule or pellet of the composition in a material, the capsule or pellet can be introduced into a volume of water, and if present the water soluble material can solubilize, degrade, or disperse to allow contact of the composition concentrate with the water. For the purposes of this disclosure, the terms "capsule" and "pellet" are used for exemplary purposes and are not intended to limit the delivery mode of the invention to a particular shape.

When provided as a liquid concentrate composition, the concentrate can be diluted through dispensing equipment using aspirators, peristaltic pumps, gear pumps, mass flow meters, and the like. This liquid concentrate embodiment can also be delivered in bottles, jars, dosing bottles, bottles with dosing caps, and the like. The liquid concentrate composition can be filled into a multi-chambered cartridge insert that is then placed in a spray bottle or other delivery device filled with a pre-measured amount of water.

In yet another embodiment, the concentrate composition can be provided in a solid form that resists crumbling or other degradation until placed into a container. Such container may either be filled with water before placing the composition concentrate into the container, or it may be filled with water after the composition concentrate is placed into the container. In either case, the solid concentrate composition dissolves, solubilizes, or otherwise disintegrates upon contact with water. In a particular embodiment, the solid concentrate composition dissolves rapidly thereby allowing the concentrate composition to become a use composition and further allowing the end user to apply the use composition to a surface in need of cleansing. When the cleansing composition is provided as a solid, the compositions provided herein may be altered in a manner to solidify the cleansing composition by any means known in the art. For example, the amount of water may be reduced or additional ingredients may be added to the cleansing composition, such as a solidification agent.

In another embodiment, the solid concentrate composition can be diluted through dispensing equipment whereby water is sprayed at the solid block forming the use solution. The water flow is delivered at a relatively constant rate using mechanical, electrical, or hydraulic controls and the like. The solid concentrate composition can also be diluted through dispensing equipment whereby water flows around the solid block, creating a use solution as the solid concentrate dissolves. The solid concentrate composition can also be diluted through pellet, tablet, powder and paste dispensers, and the like.

EXAMPLES

The present invention is more particularly described in the following examples that are intended as illustrations only, since numerous modifications and variations within the scope of the present invention will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

Materials used in the described embodiments include, but are not limited to: Stearyldimonium-hydroxypropyl Laurylglucosides Chloride, Cocoglucosides Hydroxypropyl-trimonium Chloride, Laurylglucosides Hydroxypropyl-trimonium Chloride, Poly (Lauryldimonium-hydroxypropyl Decylglucosides Chloride), Poly (Stearyldimonium-hydroxypropyl Decylglucosides Chloride), Poly (Stearyldimonium-hydroxypropyl Laruylglucosides Chloride), Poly (Trimonium-hydroxypropyl Cocoglucosides Chloride).

The following methods were used in the preparation and testing of the examples:

Antimicrobial and Microbial Efficacy:

(a) Determination of Time Kill Activity: The activity of antimicrobial compositions was measured by the time kill method [ASTM E 2315 *Standard Guide for Assessment of Antimicrobial Activity Using a Time Kill Procedure*], whereby the survival of challenged organisms exposed to an antimicrobial test composition is deterred as a function of time. In this test, a diluted aliquot of the composition is brought into contact with a known population of test bacteria for a specified time period at a specified temperature. The test composition is neutralized at the end of the time period, which arrests the antimicrobial activity of the composition. The percent or, alternatively, log reduction from the original bacteria population is calculated. In general, the time kill method is known to those skilled in the art. In addition, comparative data on the foam profile of representative systems is shown.

(b) The composition can be tested at any concentration from 0-100%. The choice of which concentration to use is at the discretion of the investigator, and suitable concentrations are readily determined by those skilled in the art. All testing if performed in triplicate, the results are combined, and the average log reduction is reported.

(c) The choice of contact time period also is at the discretion of the investigator. Any contact time period can be chosen. Typical contact times range from 15 second to 5 minutes, with 30 seconds and 1 minute being typical contact times. The contact temperature also can be any temperature, typically room temperature, or about 25 degrees Celsius.

(d) The microbial suspension, or test inoculum, is prepared by growing a microbial culture on any appropriate solid media (e.g., agar). The microbial population then is washed from the agar with sterile physiological saline and the population of the microbial suspension is adjusted to about $10^8$ colony forming units per ml (cfu/ml).

(e) The table below lists the test microbial cultures used in the following tests and includes the name of the bacteria, the ATCC (American Type Culture Collection) identification number, and the abbreviation for the name of the organism used hereafter.

| Organism Name | ATCC # | Abbreviation |
|---|---|---|
| S. aureusylococcus | 6538 | S. aureus |
| Escherichia coli | 112229 | E. coli |

S. aureus is a Gram positive bacteria, whereas, E. coli is a Gram negative bacteria.

The log reduction is calculated using the formula:

Log reduction=$\log_{10}$(numbers control)−$\log_{10}$(test sample survivors).

Foam Height Determination

The foam height was determined with the following procedural steps:
1. Prepare a 1% solution of the product in 5 grain water.
2. Pour 150 mL of the solution into a blender
3. Mix on medium speed 10 seconds.
4. Pour into a 1000 mL beaker and measure foam height.
5. Measure foam height at 3 and 5 minutes.

Foam Stability Determination

The foam stability was determined by using the difference between the foam/air interference and the foam/aqueous interface 5 minutes after pouring a 1% solution into a 1000 mL beaker.

In Vitro Irritancy Determination

In vitro irritancy was assessed by an external testing facility using Matek Corporation's "EpiDerm MTT ET-50 Protocol (EPI-200)".

The test consists of a topical exposure of the neat test chemical to a reconstructed human epidermis (RhE) model followed by a cell viability test. Cell viability is measured by dehydrogenase conversion of MTT [(3-4,5-dimethyl thiazole 2-yl) 2,5-diphenyltetrazolium bromide], present in cell mitochondria, into a blue formazan salt that is quantitatively measured after extraction from tissues. The reduction of the viability of tissues exposed to chemicals in comparison to negative controls (treated with water) is used to predict the skin irritation potential.

EpiDerm tissues are conditioned by incubation of release transport-stress related compounds and debris overnight. After pre-incubation, tissues are topically exposed to the test chemicals for 60 minutes. Preferably, three tissues are used per test chemical (TC) and for the positive control (PC) and negative control (NC). Tissues are then thoroughly rinsed, blotted to remove the test substances, and transferred to fresh medium. Tissues are incubated for 42 hrs. Afterwards, the MTT assay is performed by transferring the tissues to 24-well plates containing MTT medium (1 mg/mL) after a 3 hr MTT incubation, the blue formazan salt formed by cellular mitochondria is extracted with 2.0 mL/tissue of isopropanol and the optical density of the extracted formazan is determined using a spectrophotometer at 570 nm. Relative cell viability is calculated for each tissue as % of the mean of the negative control tissues. Skin irritation potential of the test material is predicted if the remaining relative cell viability is below 50%.

Foam Resistance Determination

The foam resistance was determined by measuring 65 grams of the test product into a blender and blending for about 10 seconds on medium speed. Thereafter, the test solution was poured into a cylinder and a plastic ball was dropped into the test solution and timed to determine how many seconds it took for the plastic ball to drop from a first pre-determined level to a second pre-determined level, e.g., from 100 mL mark on the cylinder to the 40 mL mark on the cylinder.

The following Figures demonstrate efficacy data of the present antimicrobial composition, using various cationic active ingredients, quaternary sugar-derived surfactants and optional foam boosting surfactants.

Table 7 and FIG. 1 (Log Kill of Cationic Active Ingredients): The following figures illustrate the efficacy following a 30 second exposure time of three different cationic active ingredients, specifically, 0.5% Quat (Benzalkonium Chloride), 2% CHG (Chlorhexidine Gluconate), and 1% PHMB (polyhexamethylene biguanide) in a representative surfactant system.

Table 7 illustrates the formulas for the three cationic active ingredient systems tested. Both the quaternary sugar-derived surfactant and foam boosting surfactant were held constant and only the cationic active ingredient was changed between the three tests performed. The results are illustrated in FIG. 1.

TABLE 7

| Active Ingredient System | Ingredients | Level (% w/w) |
|---|---|---|
| Quaternary Ammonium Compound (Quat) | Active Ingredient | 0.5 |
| | Quaternized Sugar-Derived Surfactant | 1.25 |
| | Foam Boosting Agent | 1.95 |
| Chlorhexidine Gluconate (CHG) | Active Ingredient | 2.0 |
| | Quaternized Sugar-Derived Surfactant | 1.25 |
| | Foam Boosting Agent | 1.95 |
| Poly Hexamethylene Biguanide (PHMB) | Active Ingredient | 1.0 |
| | Quaternized Sugar-Derived Surfactant | 1.25 |
| | Foam Boosting Agent | 1.95 |

As illustrated in FIG. 1, all three cationic active ingredients had high cidal activity against *S. aureus* and *E. coli* bacteria within a 30 second exposure time.

Figure 2:
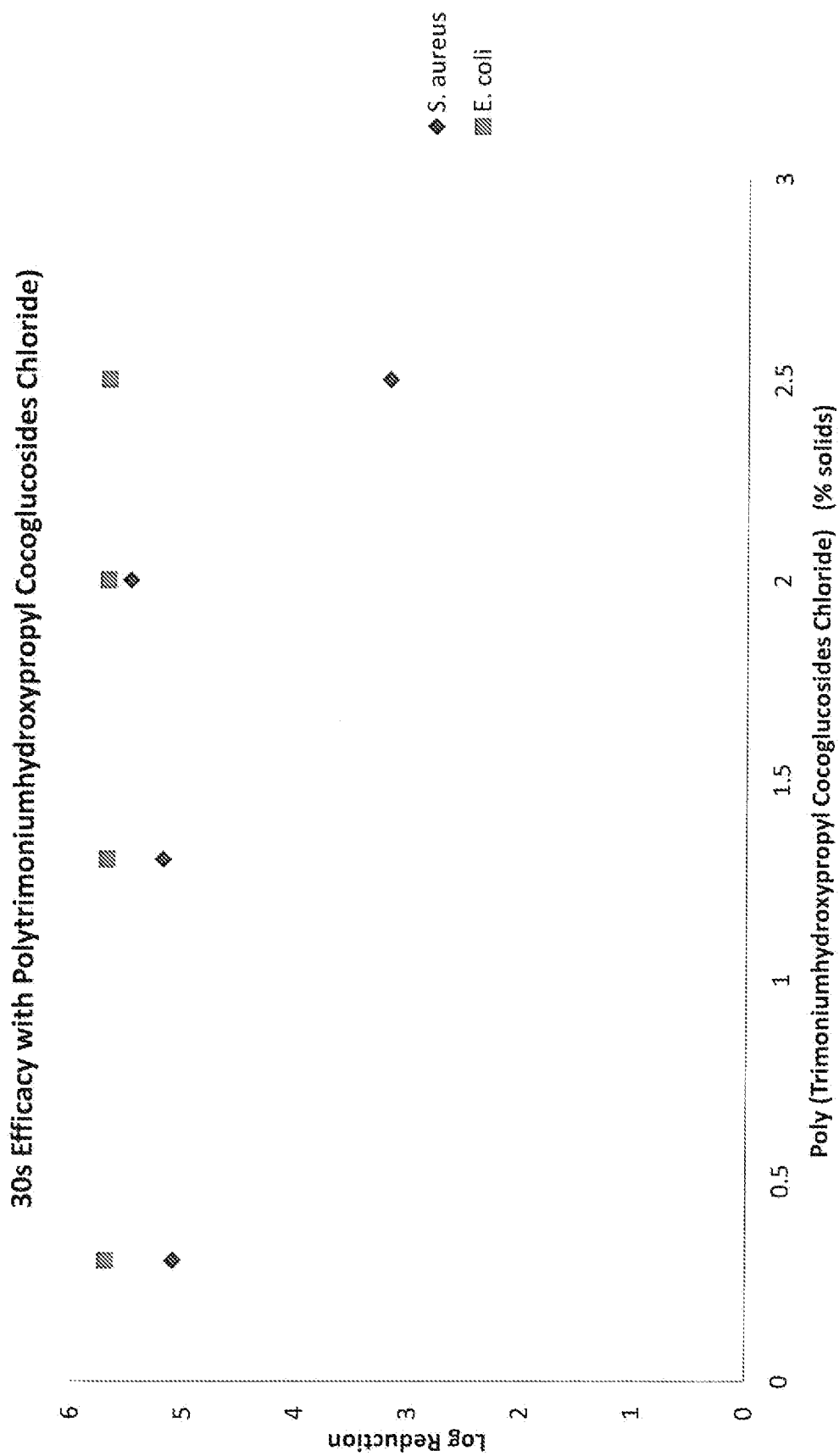
FIG. 2 illustrates a graph depicting the test results of the efficacy against S. aureus and E. coli bacteria with increased concentrations of quaternary sugar-derived surfactants, specifically, poly (trimoniumhydroxypropyl cocogluocosides chloride). The amount and type of cationic active ingredient (0.5% ADBAC) and foam boosting surfactant (1.95% alkyl dimethyl amine oxide) was held constant.

Table 8 and FIG. 2 (Log Kill of Quaternary Sugar-Derived Surfactants): Next, Applicants tested the efficacy against *S. aureus* and *E. coli* bacteria with increased concentrations of quaternary sugar-derived surfactants, specifically, Poly (Trimoniumhydroxypropyl Cocogluocosides Chloride). The amount and type of cationic active ingredient (0.5% ADBAC Quat) and foam boosting surfactant (1.95% Alkyl Dimethyl Amine Oxide) was held constant. Table 8 below illustrates the quantitative results of this test and FIG. 2 illustrates the graphical results.

TABLE 8

| Quaternized Sugar-Derived Surfactant (% w/w) | Active Ingredient (% w/w) | Foam Boosting Agent (% w/w) | S. aureus Log Reduction | E. coli Log Reduction |
|---|---|---|---|---|
| 0.3 | 0.5 | 1.95 | >5.0 | >5.0 |
| 1.3 | 0.5 | 1.95 | >5.0 | >5.0 |
| 2.5 | 0.5 | 1.95 | 3.2 | >5.0 |

As Table 8 and FIG. 2 illustrate, the quaternary sugar-derived surfactant has a high cidal activity against *S. aureus* and *E. coli* bacteria after only 30 seconds of exposure. Also, the tolerance of the quaternary sugar derived surfactant against bacteria is shown. Furthermore, it is clearly illustrated that an increased concentration of quaternary sugar-derived surfactant maintains a good log kill of bacteria up until a 1 to 4 ratio of quaternary sugar-derived surfactant to cationic active ingredients.

Figure 3:
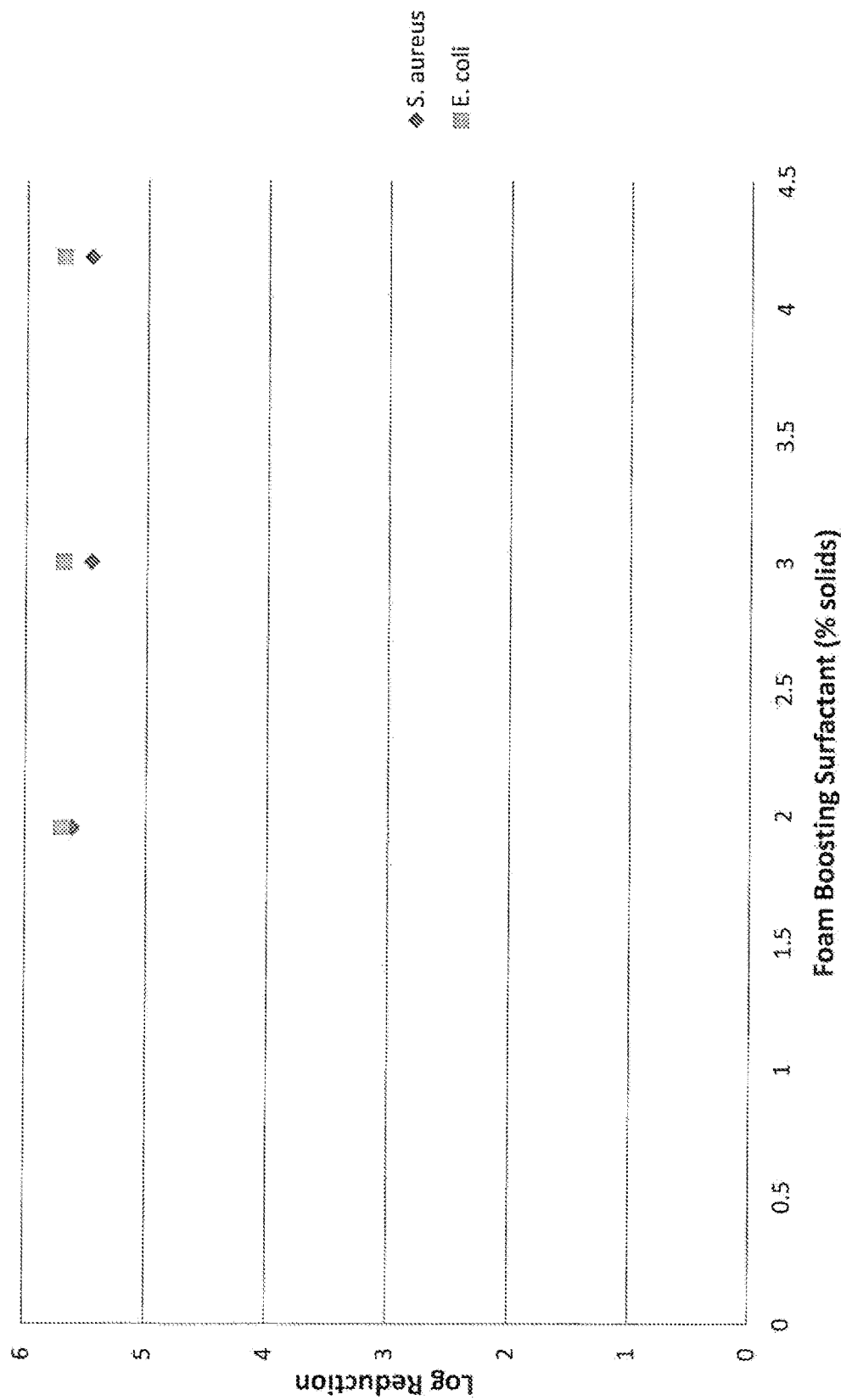
FIG. 3 illustrates a graph depicting the test results of the efficacy with increased concentrations of foam boosting surfactants, specifically, amine oxide. The amount and type of cationic active ingredient (0.5% ADBAC) and quaternary sugar-derived surfactant (1.25% poly trimoniumhydroxypropyl cocoglucosides chloride) were held constant.

Table 9 and FIG. 3 (Log Kill of Foam Boosting Surfactants): Table 15 and FIG. 3 illustrate the efficacy with increased concentrations of foam boosting surfactants, specifically, amine oxide. The amount and type of cationic active ingredient (0.5% ADBAC Quat) and Quaternary sugar-derived surfactant (1.25% Poly Trimoniumhydroxypropyl Cocoglucosides Chloride) were held constant. Table 9 below illustrates the quantitative results of this test and FIG. 3 illustrates the graphical results.

TABLE 9

| Foam Boosting Agent (% w/w) | Active (% w/w) | Quaternized Sugar-Derived Surfactant (% w/w) | S. aureus Log Reduction | E. coli Log Reduction |
|---|---|---|---|---|
| 1.95 | 0.5 | 1.25 | >5.5 | >5.5 |
| 3.0 | 0.5 | 1.25 | >5.5 | >5.5 |
| 4.2 | 0.5 | 1.25 | >5.5 | >5.5 |

As Table 9 and FIG. 3 illustrate, the foam boosting surfactant has a high cidal activity against *S. aureus* and *E. coli* bacteria after only 30 seconds of exposure. Also, the tolerance of the foam boosting surfactant against bacteria is shown. Furthermore, it is clearly illustrated that a broad range of foam boosting surfactant maintains a good log kill of bacteria.

Figure 4:
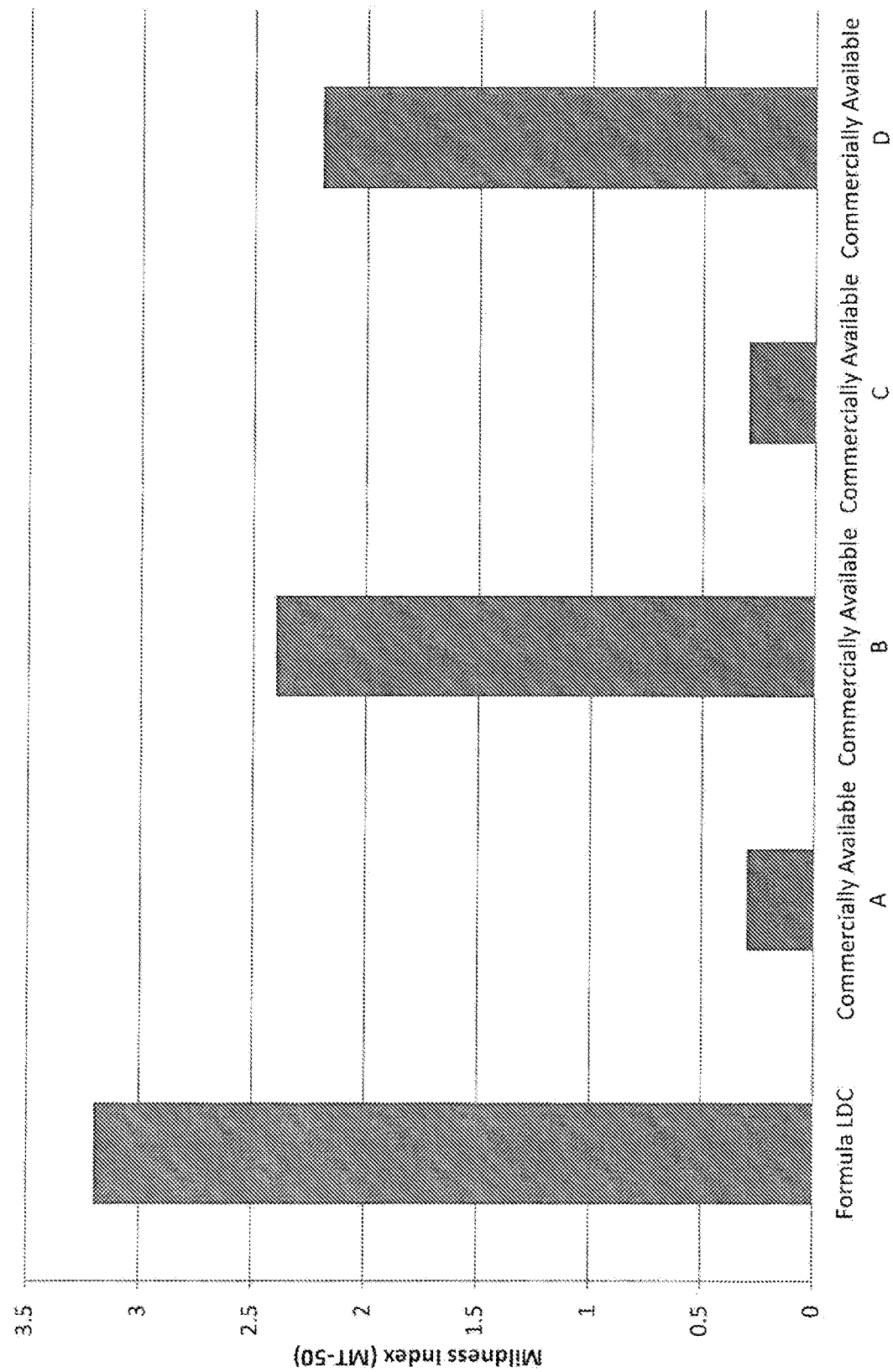
FIG. 4 illustrates the dermal irritancy (mildness) of the preferred embodiment for an antimicrobial dermal cleanser to four commercially available antimicrobial soaps.

FIG. 4 (Mildness Index for an Antimicrobial Dermal Cleanser Embodiment): Applicants tested the dermal irritancy (mildness) of the preferred embodiment for an antimicrobial Dermal Cleanser as illustrated in Table 12 to four commercially available antimicrobial soaps. Commercially Available Products A, C and D are available by Gojo Medicated, Akron, Ohio and Commercially Available Product B is available by Dial a subsidiary of Henkel Corporation, Dusseldorf, Germany. As illustrated in FIG. 4, the antimicrobial dermal cleanser of the current invention has a high relative mildness index especially in comparison to antimicrobial hand soaps that are commercially available.

Figure 5:
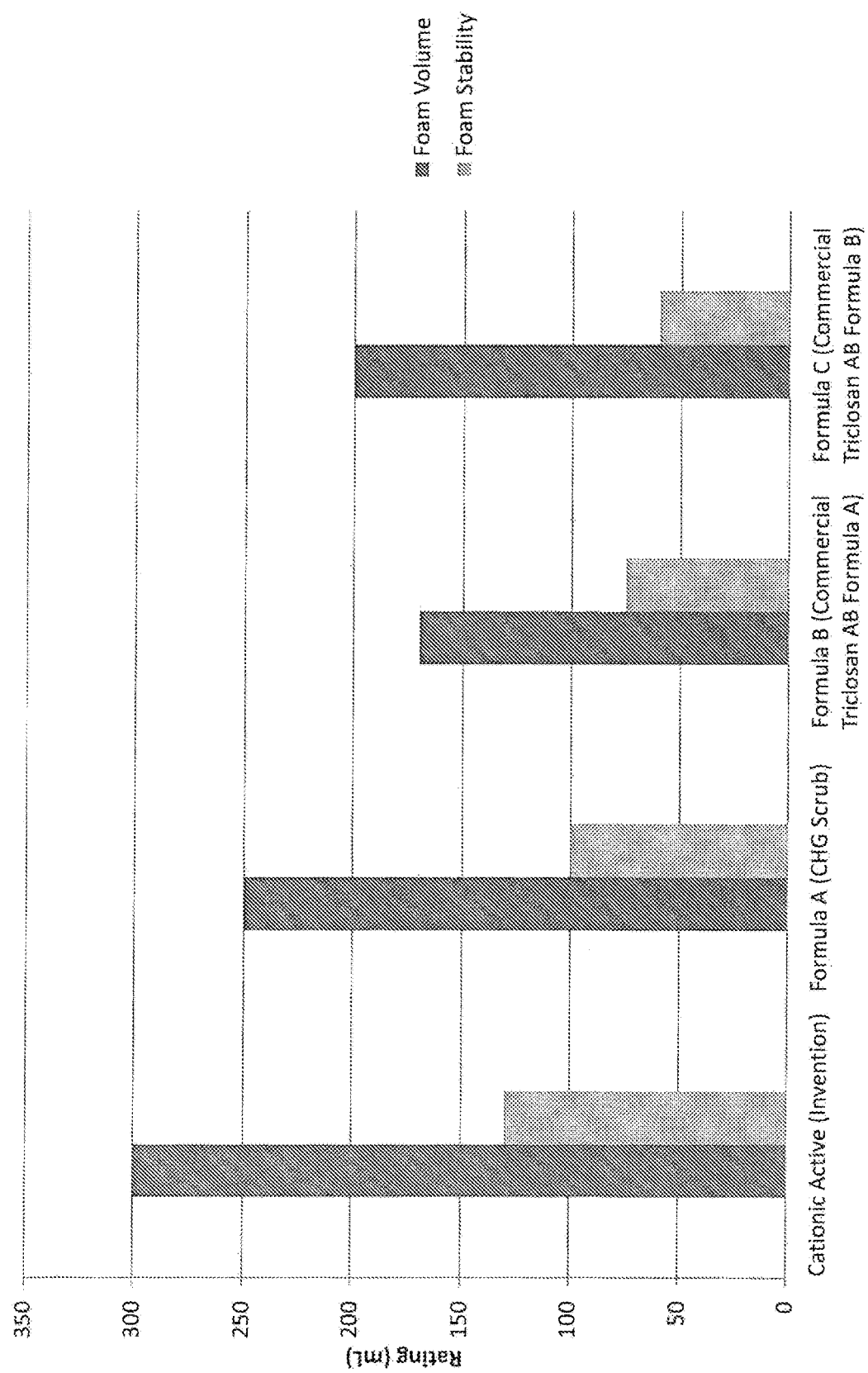
FIG. 5 illustrates the foam profile of the preferred embodiment for an antimicrobial dermal cleanser to three commercially available antimicrobial soaps.
Figure 6:
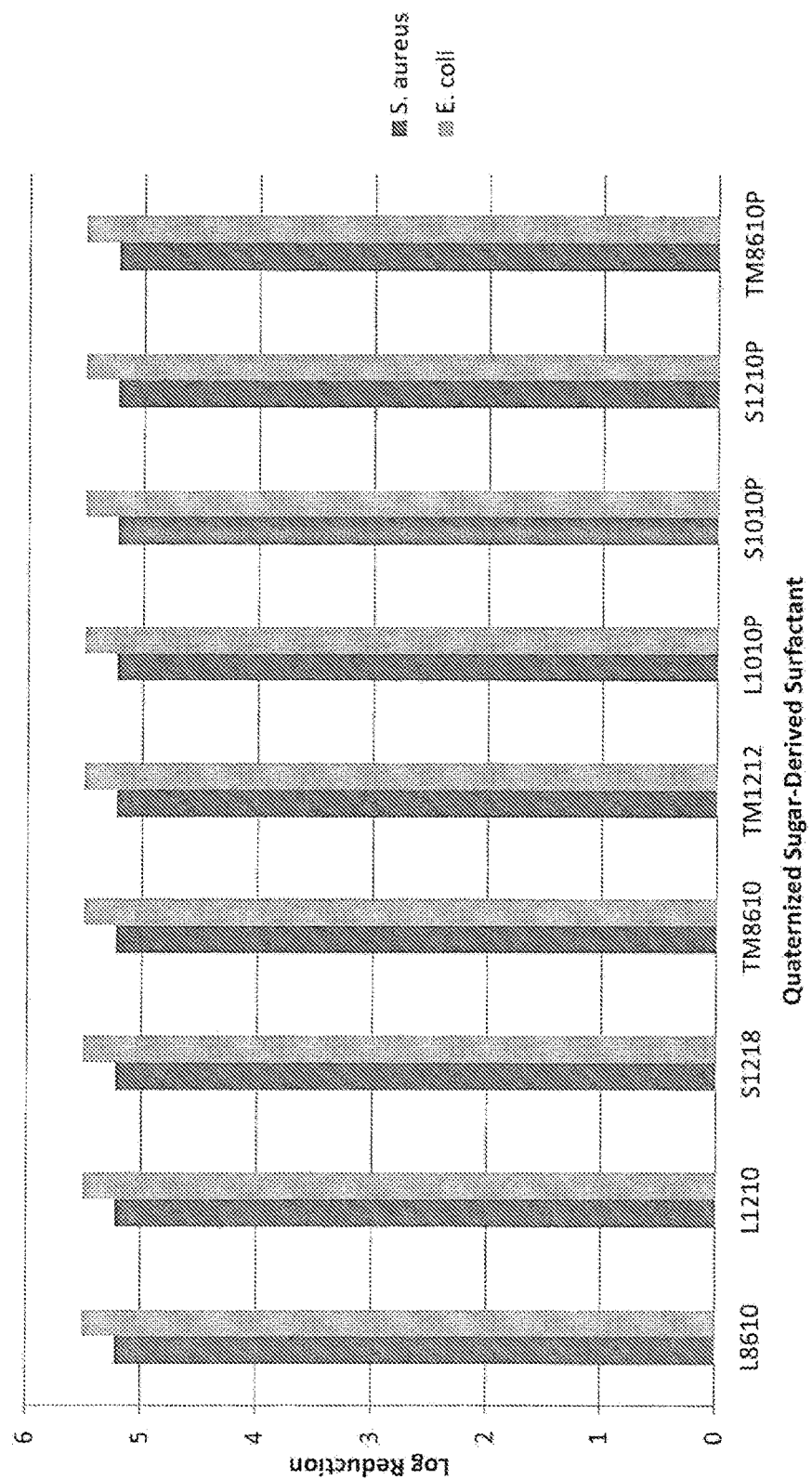
FIG. 6 illustrates the efficacy against S. aureus and E. coli bacteria following a 30 second exposure to a cationic active in combination with quaternary sugar-derived surfactants, held constant at 1.25% and an n-alkyl ($C_{12-16}$) dimethylamine oxide foam boosting surfactant.

FIG. 5 (Foam Profile for an Antimicrobial Dermal Cleanser Embodiment): Applicants tested the foam profile of the preferred embodiment for an antimicrobial Dermal Cleanser as illustrated in Table 12 to three commercially available antimicrobial soaps. As illustrated in FIG. 6, the antimicrobial dermal cleanser of the current invention has both good foam volume and foam stability especially in comparison to antimicrobial hand soaps that are commercially available.

Table 10 and FIG. 6 (Efficacy of Cationic Actives in Combination with Quaternary Sugar Derived Surfactants and Alkyl Dimethyl Amine Oxide): Applicants tested the efficacy against *S. aureus* and *E. coli* bacteria with various quaternary sugar-derived surfactants, held constant at 1.25%. The amount and type of cationic active ingredient (0.5% ADBAC Quat) and foam boosting surfactant (1.95% Alkyl Dimethyl Amine Oxide) was held constant.

TABLE 10

| Quaternized Sugar-Derived Surfactant (1.25% w/w) | Active Ingredient (%w/w) | Foam Boosting Surfactant (% w/w) | S. aureus Log Reduction | E. coli Log Reduction |
|---|---|---|---|---|
| (L8610) Lauridimonium-hydroxypropyl Cocoglucosides Chloride | 0.5 | 1.95 | >5.0 | >5.0 |
| (L1210) Lauridimonium-hydroxypropyl Laurylglucosides Chloride | 0.5 | 1.95 | >5.0 | >5.0 |
| (S1218) Stearyldimonium-hydroxypropyl Laurylglucosides Chloride | 0.5 | 1.95 | >5.0 | >5.0 |
| (TM8610) Cocoglucosides Hydroxypropyl-trimonium Chloride | 0.5 | 1.95 | >5.0 | >5.0 |
| (TM1212) Laurylglucosides Hydroxypropyl-trimonium Chloride | 0.5 | 1.95 | >5.0 | >5.0 |
| (L1010P) Poly (Lauryldimonium-hydroxypropyl Decylglucosides Chloride) | 0.5 | 1.95 | >5.0 | >5.0 |

TABLE 10-continued

| Quaternized Sugar-Derived Surfactant (1.25% w/w) | Active Ingredient (%w/w) | Foam Boosting Surfactant (% w/w) | S. aureus Log Reduction | E. coli Log Reduction |
|---|---|---|---|---|
| (S1010P) Poly (Stearyldimonium-hydroxypropyl Decylglucosides Chloride) | 0.5 | 1.95 | >5.0 | >5.0 |
| (S1210P) Poly (Stearyldimonium-hydroxypropyl Laruylglucosides Chloride) | 0.5 | 1.95 | >5.0 | >5.0 |
| (TM8610P) Poly (Trimonium-hydroxypropyl Cocoglucosides Chloride) | 0.5 | 1.95 | >5.0 | >5.0 |

As Table 10 illustrates, a high log kill is maintained against *S. aureus* and *E. coli* bacteria for both quaternized sugar-derived surfactants and polyquaternized sugar-derived surfactants. The chain length of the sugar quaternary surfactant may be altered and yet still maintain high efficacy. The graphical results of the test are illustrated in FIG. 6.

Figure 7:
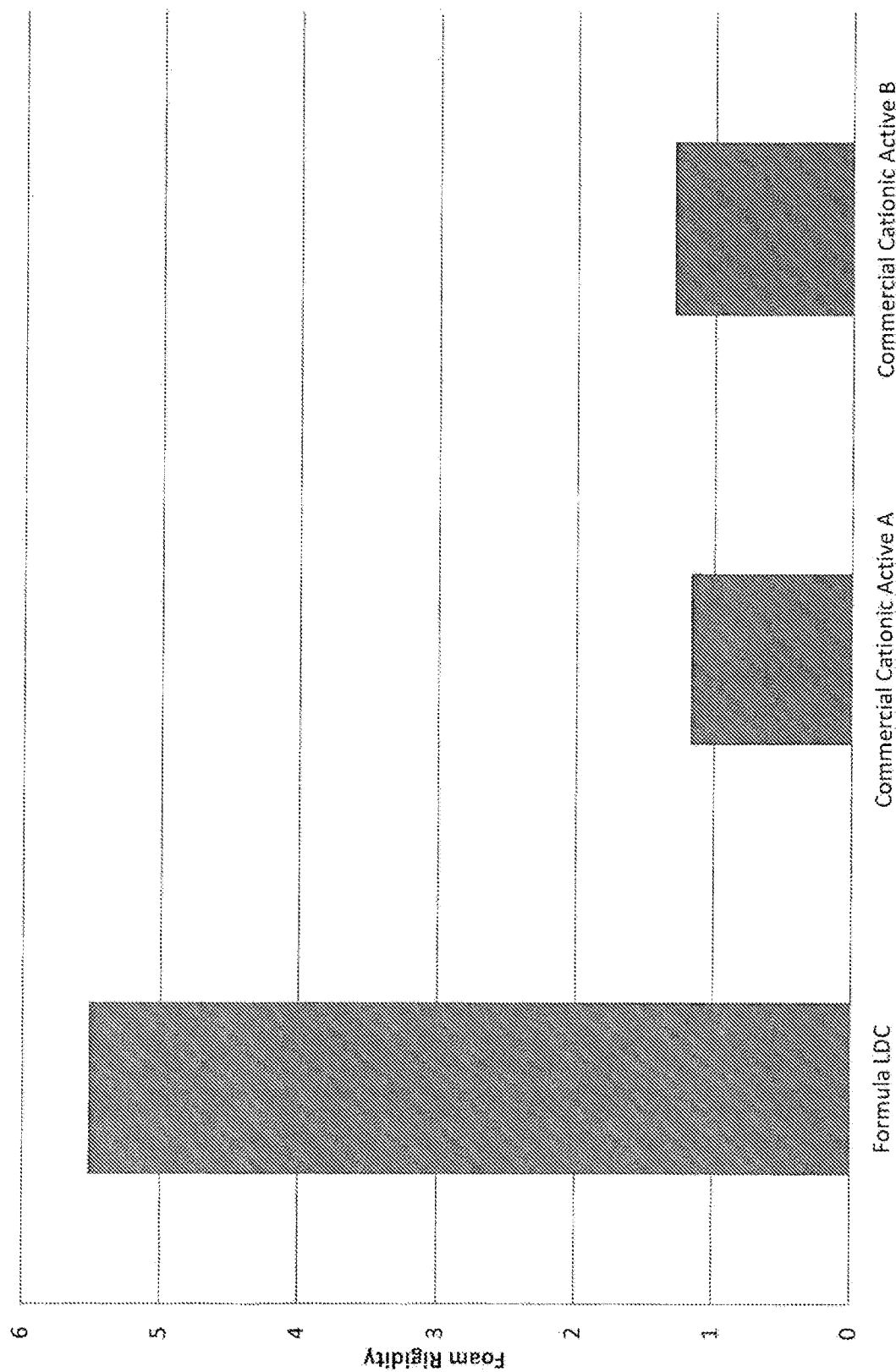
FIG. 7 illustrates the foam rigidity of the preferred embodiment for an antimicrobial dermal cleanser to two commercially available antimicrobial soaps with cationic actives.

Table 11 and FIG. 7 (Comparative Foam Rigidity): Applicants tested the foam rigidity of an embodiment of the current invention for use in dermal applications as shown below in Table 11 in comparison to two commercially available products, Commercial Products E and F. Commercial Products E and F are traditional anionic surfactant base dermal washes containing a cationic active. Commercial Product E is commercially available by Proctor & Gamble, Cincinnati, Ohio and Commercial Product F is commercially available by Deb Group Limited, United Kingdom, England. The results of the foam rigidity test are illustrated in FIG. 7. As illustrated in FIG. 7, the foam rigidity of the dermal wash of the current invention is greater than commercially available cationic active dermal washes with a traditional anionic surfactant base.

Foam Rigidity Formula of Current Invention (pH of 5.5-7.5):

TABLE 11

| Component | Weight Percent |
|---|---|
| Water | 91.7 |
| Cationic Active (Quaternary Ammonium Compound) | 0.5 |
| Quaternized Sugar-Derived Surfactant | 0.7 |
| Foam Boosting Surfactant | 4.1 |
| Dermal Adjuvants | 3.0 |

Table 12 (Antimicrobial Efficacy of a Dermal Cleanser of the Current Invention): Applicants tested the efficacy of the dermal cleanser of the current invention by determining the log reduction of both gram positive and gram negative bacterial after 30 seconds of exposure.
Dermal Cleanser of Current Invention (pH of 5.5-7.5):

TABLE 12

| Component | Weight Percent Range |
|---|---|
| Water | 7.5-99.3 |
| Cationic Active (Quaternary Ammonium Compound) | 0.3-5 |
| Quaternized Sugar-Derived Surfactant | 0.05-7.5 |
| Foam Boosting Surfactant | 0.2-5 |
| Dermal Adjuvants | 0.1-7 |

Table 13 (Antimicrobial Efficacy of a Surgical Scrub of the Current Invention): Applicants tested the efficacy of the surgical scrub of the current invention by determining the log reduction of both gram positive and gram negative bacterial after 30 seconds of exposure.
Surgical Scrub of Current Invention (pH of 5.5-7.5):

TABLE 13

| Component | Weight Percent Range |
|---|---|
| Water | 56-97.8 |
| Cationic Active (Quaternary Ammonium Compound) | 1-6 |
| Quaternized Sugar-Derived Surfactant | 0.2-8 |
| Foam Boosting Surfactant | 0.5-10 |
| Dermal Adjuvants | 0.5-20 |

The antimicrobial compositions of the present invention have several practical end uses, including hand cleansers, surgical scrubs, hand sanitizer gels, and similar personal care products. Additional types of compositions include foamed compositions, such as creams, mousses, and the like. The present antimicrobial compositions can be manufactured as dilute ready-to-use compositions, or as concentrates that are diluted prior to use.

Obviously, many modifications and variations of the invention as hereinbefore set forth can be made without departing from the spirit and scope thereof, and, therefore, only such limitations should be imposed as are indicated by the appended claims.

We claim:

1. An antimicrobial dermal cleanser comprising:
   (a) about 0.3 wt. % to about 5.0 wt. % of a cationic active antimicrobial ingredient; wherein the cationic active antimicrobial ingredient is alkyl dimethyl benzyl ammonium chloride;
   (b) less than 2.5 wt. % of a quaternized sugar-derived surfactant, wherein the quaternized sugar-derived surfactant is laurdimonium-hydroxypropyl cocoglucoside chloride, laurdimonium-hydroxypropyl laurylglucosides chloride, stearyldimoniuhydroxypropyl laurylglucosides chloride, cocoglucosides hydroxypropyltrimonium chloride, lauryl glucosides hydroxypropyltrimonium chloride, poly (lauryldimonium hydroxypropyl decylglucosides chloride), poly (stearyldimonium hydroxypropyl decylglucosides chloride), poly (stearyldimonium hydroxypropyl laruylglucosides chloride), poly (trimonium hydroxypropyl cocoglucosides chloride); or mixtures thereof
   (c) 0.2 wt. % to 5.0 wt. % of a foam boosting surfactant, wherein the foam boosting surfactant is alkyl dimethyl amine oxide; and
   (d) water as a carrier;
   wherein the composition is free of triclosan (2,4,4"-trichloro-2"-hydroxy-diphenylether);
   wherein the cleanser is free of an anionic surfactant; and
   wherein the relative weight ratio of the cationic active antimicrobial ingredient to the quaternized sugar-derived surfactant to the foam boosting surfactant is from about 1:0.2:0.2 to 1:3:8.

2. The antimicrobial composition of claim 1, wherein the composition or a use solution of the composition has a pH range from about 4.0 to about 9.0.

3. The antimicrobial composition of claim 1, wherein the composition further comprises about 1 wt. % to about 25 wt. % of glycerin, sorbitol esters, polyquats, preservatives, or a combination thereof.

4. The antimicrobial composition of claim 1, wherein the composition exhibits an at least five log kill against *S. aureus* and *E. coli*.

5. The antimicrobial composition of claim 1, wherein the composition provides foam stability.

6. The antimicrobial composition of claim 1, wherein the composition improves skin compatibility and skin health.

7. The antimicrobial composition of claim 1, wherein the composition exhibits reduced tissue irritancy potential.

8. An antimicrobial surgical scrub, consisting essentially of:
  (e) about 0.5 wt. % to about 6.0 wt. % of a cationic active antimicrobial ingredient; wherein the active antimicrobial ingredient is alkyl dimethyl benzyl ammonium chloride;
  (f) less than 2.5 wt. % of a quaternized sugar-derived surfactant, wherein the quaternized sugar-derived surfactant is lauridimonium-hydroxypropyl cocoglucosides chloride, lauridimonium-hydroxypropyl laurylglucosides chloride, stearyldimonium-hydroxypropyl laurylglucosides chloride, cocoglucosides hydroxypropyl-trimonium chloride, laurylglucosides hydroxypropyl-trimonium chloride, poly (lauryl dimonium-hydroxypropyl decylglucosides chloride), poly (stearyldimonium-hydroxypropyl decylglucosides Chloride), poly (stearyldimonium-hydroxypropyl laruylglucosides chloride), and/or poly (trimonium-hydroxypropyl cocoglucosides chloride);
  (g) 0.5 wt. % to 10 wt. % of a foam boosting surfactant, wherein the foam boosting surfactant is alkyl dimethyl amine oxide; and
  (h) water as a carrier;
  wherein the composition is free of triclosan (2,4,4"-trichloro-2"-hydroxy-diphenylether); and
  wherein the cleanser is free of an anionic surfactant; and
  wherein the relative weight ratio of the cationic active antimicrobial ingredient to quaternized sugar-derived surfactant to the foam boosting surfactant is from about 1:0.2:0.2 to 1:3:8.

9. A method of reducing bacterial, microbial, fungicidal or viral population on a dermal tissue of a mammal comprising the step of contacting the dermal tissue of a mammal with the composition of claim 1 for a sufficient time to provide substantial bacterial, microbial, fungicidal or viral reduction.

10. The method of claim 9 wherein the sufficient contact time is approximately about 1 to about 60 seconds.

11. The method of claim 9 wherein the composition of claim 1 is rinsed off of a dermal tissue of a mammal after contact or remains on the dermal tissue of a mammal after contact.

12. The method of claim 9, wherein the composition has a pH range from about 4.0 to about 9.0.

13. The method of claim 9, wherein the composition further comprises about 1 wt. % to about 25 wt. % of glycerin, sorbitol esters, polyquats, preservatives, or combination thereof.

14. The method of claim 9, wherein the composition exhibits high cidal activity.

15. The method of claim 9, wherein the composition provides copious foam and foam stability.

16. The method of claim 9, wherein the composition improves skin compatibility and skin health.

17. The method of claim 9, wherein the composition exhibits reduced tissue irritancy potential.

* * * * *

UNITED STATES PATENT AND TRADEMARK OFFICE
CERTIFICATE OF CORRECTION

PATENT NO. : 10,624,826 B2
APPLICATION NO. : 14/748848
DATED : April 21, 2020
INVENTOR(S) : Eder et al.

It is certified that error appears in the above-identified patent and that said Letters Patent is hereby corrected as shown below:

In the Claims

In Claim 1, Column 20, Line 48:
DELETE: "stearyldimoniuhydroxypropyl"
INSERT: --stearyldimoniumhydroxypropyl--

In Claim 8, Column 21, Line 26:
DELETE: "lauridimonium-"
INSERT: --laurdimonium- --

In Claim 8, Column 21, Line 27:
DELETE: "lauridimonium-"
INSERT: --laurdimonium- --

Signed and Sealed this
Thirtieth Day of June, 2020

Andrei Iancu
*Director of the United States Patent and Trademark Office*